(12) United States Patent
Bhole et al.

(10) Patent No.: US 11,014,840 B2
(45) Date of Patent: May 25, 2021

(54) PROCESS CONDENSATE WATER TREATMENT

(71) Applicant: Ecolab USA Inc., St. Paul, MN (US)

(72) Inventors: Yogesh Bhole, Pune (IN); Seong-Hoon Yoon, Naperville, IL (US); Manish Kumar Singh, Pune (IN)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 16/047,678

(22) Filed: Jul. 27, 2018

(65) Prior Publication Data

US 2019/0031543 A1 Jan. 31, 2019

Related U.S. Application Data

(60) Provisional application No. 62/539,026, filed on Jul. 31, 2017.

(51) Int. Cl.
*C02F 9/00* (2006.01)
*C02F 3/32* (2006.01)
(Continued)

(52) U.S. Cl.
CPC .............. *C02F 3/327* (2013.01); *C02F 1/441* (2013.01); *C02F 3/1268* (2013.01); *C02F 3/347* (2013.01); *C02F 9/00* (2013.01); *C12P 1/00* (2013.01); *C02F 1/20* (2013.01); *C02F 1/283* (2013.01); *C02F 1/42* (2013.01); *C02F 1/66* (2013.01); *C02F 2001/427* (2013.01);
(Continued)

(58) Field of Classification Search
None
See application file for complete search history.

(56) References Cited

U.S. PATENT DOCUMENTS 4,952,751 A    8/1990   Blume et al.
5,970,420 A * 10/1999   Scott .................... F42B 33/062
                                                                  588/312
(Continued)

FOREIGN PATENT DOCUMENTS

CA           2137754 A1    6/1995
CN        201567252 U    9/2010
(Continued)

OTHER PUBLICATIONS

Al-Derham, "Study to Treat and Re-use Treated Industrial and Process Water," F23—Energy efficient technologies ensuring environmental sustainability of the oil and gas industry, 21st World Petroleum Congress, Moscow, 8 pp. (2014).

(Continued)

Primary Examiner — Chester T Barry
(74) Attorney, Agent, or Firm — Leydig, Voit & Mayer, Ltd.

(57) ABSTRACT

Methods of and systems for removing organic substance from condensate generated from an industrial evaporation process are provided. The condensate comprises water and the organic substance. The methods and systems provide solutions related to enthalpy recovery of industrial evaporation processes such as, for example, sugar cane juice evaporation processes, dairy evaporation processes, coffee processing evaporation processes, fruit juice evaporation processes, soup evaporation processes, and chemical industry evaporation processes.

16 Claims, 2 Drawing Sheets

(51) Int. Cl.
*C02F 3/34* (2006.01)
*C02F 1/44* (2006.01)
*C12P 1/00* (2006.01)
*C02F 3/12* (2006.01)
C02F 101/32 (2006.01)
C02F 101/34 (2006.01)
C02F 1/66 (2006.01)
C02F 1/42 (2006.01)
C02F 1/28 (2006.01)
C02F 103/32 (2006.01)
C02F 1/20 (2006.01)

(52) U.S. Cl.
CPC .... *C02F 2101/322* (2013.01); *C02F 2101/34* (2013.01); *C02F 2103/32* (2013.01); *C02F 2301/10* (2013.01); *C02F 2305/06* (2013.01)

(56) References Cited

U.S. PATENT DOCUMENTS

| | | |
|---|---|---|
| 6,110,376 A | 8/2000 | Savage et al. |
| 8,029,671 B2 | 10/2011 | Cath et al. |
| 8,216,474 B2 | 7/2012 | Cath et al. |
| 8,496,832 B2 | 7/2013 | Al-Jlil |
| 2002/0011246 A1* | 1/2002 | Reisig ............... C13B 10/00 127/54 |
| 2002/0015772 A1* | 2/2002 | Munch ............... A23L 2/64 426/478 |
| 2010/0072130 A1* | 3/2010 | Fane ............... C02F 1/04 210/605 |
| 2010/0224364 A1 | 9/2010 | Heins |
| 2011/0232343 A1 | 9/2011 | Mantelatto et al. |
| 2014/0245973 A1 | 9/2014 | Minnich |
| 2014/0246372 A1 | 9/2014 | Musale et al. |
| 2015/0232360 A1 | 8/2015 | Song et al. |
| 2015/0305370 A1 | 10/2015 | Bleyer et al. |
| 2015/0345032 A1* | 12/2015 | Smith ............ C11D 3/2086 134/7 |
| 2016/0348134 A1* | 12/2016 | Burns-Guydish ....... C12N 1/14 |

FOREIGN PATENT DOCUMENTS

| | | | |
|---|---|---|---|
| CN | 203715436 U | 7/2014 | |
| CN | 104003569 A | 8/2014 | |
| ES | 8503961 A1 * | 4/1985 | ............... B01D 3/06 |
| GB | 390343 A * | 4/1933 | ............. F01K 7/025 |
| GB | 433678 A * | 8/1935 | ............... A23C 1/12 |
| IN | 192977 A | 6/2004 | |
| WO | WO 96/16905 A1 | 6/1996 | |
| WO | WO 03/106354 A1 | 12/2003 | |
| WO | WO 2009/155675 A2 | 12/2009 | |
| WO | WO 2011/091951 A1 | 8/2011 | |
| WO | WO 2012/059429 A1 | 5/2012 | |
| WO | WO 2012/059430 A1 | 5/2012 | |
| WO | WO 2015/190907 A1 | 12/2015 | |

OTHER PUBLICATIONS

Gavach et al., "Assessing Reverse Osmosis for Water Recycling in Alcoholic Fermentation Processes," *International Journal of Chemical Reactor Engineering*, vol. 7, article A73, 12 pp. (2009).

Hao et al., "New technique of sugar-removing from the condensate in sugarcane mills," *Guangxi Kexue*, vol. 17, No. 2, pp. 132-134 (2010).

Sagne et al., "A pilot scale study of reverse osmosis for the purification of condensate arising from distillery stillage concentration plant," *Chemical Engineering and Processing: Process Intensification*, vol. 49, pp. 331-339 (2010).

Suárez et al., "Production of high-quality water by reverse osmosis of milk dairy condensates," *Journal of Industrial and Engineering Chemistry*, vol. 21, pp. 1340-1349 (2015).

Suárez et al., "Recovery of dairy industry wastewaters by reverse osmosis. Production of boiler water," *Separation and Purification Technology*, vol. 133, pp. 204-211 (2014).

Bérubé et al., "High Temperature Biological Treatment of Foul Evaporator Condensate for Reuse," Project Report 2000-6, pp. 1-20 (Apr. 2010); downloaded from the Internet at https://era.library.ualberta.ca/items/db98227b-5606-44b6-b4e1-ea28b96cfc94/view/c598c10e-2107-4e7a-82cb-a5080b93d447/PR_2000-6.pdf on Nov. 14, 2018.

Dias et al., "Biological treatment of kraft pulp mill foul condensates at high temperatures using a membrane bioreactor," *Process Biochem.*, 40(3-4): 1125-1129 (Mar. 2005).

Liao et al., "Treatment of kraft evaporator condensate using a thermophilic submerged anaerobic membrane bioreactor," *Water Science & Tech.*, 61(9): 2177-2183 (May 2010).

Xie et al., "Performance and fouling characteristics of a submerged anaerobic membrane bioreactor for kraft evaporator condensate treatment," *Environmental Tech.*, 31(5): 511-521 (Apr. 14, 2010).

European Patent Office, International Search Report in International Patent Application No. PCT/US2018/044106, 5 pp. (dated Oct. 22, 2018).

European Patent Office, Written Opinion in International Patent Application No. PCT/US2018/044106, 15 pp. (dated Oct. 22, 2018).

* cited by examiner

PROCESS CONDENSATE WATER TREATMENT

This application is a nonprovisional application claiming the benefit of U.S. Provisional Patent Application Ser. No. 62/539,026, filed Jul. 31, 2017, the disclosure of which is incorporated herein by reference in its entirety.

TECHNICAL FIELD

The disclosure is directed to methods of and systems for removing organic substance from condensate generated from an industrial evaporation process. The methods and systems provided herein can be utilized to form purified water that can be fed into an industrial process, e.g., a steam-generating system (e.g., a boiler system).

BACKGROUND OF THE INVENTION

Generally, industrial evaporation processes are utilized to remove water from mixtures where water is present and not needed. For example, an industrial-scale soup producer may wish to remove water from soup prior to canning in order to save on shipping a relatively large quantity of water that may be added by the consumer upon preparation.

In the aforementioned example, the water removed from the soup via evaporation comprises much enthalpy, but generally further comprises substances other than water (e.g., sugar). The evaporated substance becomes enthalpy-rich condensate, which, if reasonably pure, could be utilized as a feed stream for a steam-generating system, or at least an enthalpy source to heat a feed stream of a steam-generating system.

BRIEF SUMMARY OF THE INVENTION

A method of removing organic substance from condensate generated from an industrial evaporation process is provided. The condensate comprising water and the organic substance. The method comprises combining the condensate with micronutrient and microbiological material to form treated condensate comprising water, the organic substance, the micronutrient, and the microbiological material. The organic substance and the micronutrient is reacted with the microbiological material in the treated condensate at a pH of from about 6 to about 9 to form a bioreactor product comprising byproduct and water. The water is purified from the byproduct in the bioreactor product to form purified water.

A system for removing organic substance from condensate generated by an industrial evaporation process is provided. The condensate comprising water and the organic substance. The system comprises a bioreactor configured to receive the condensate generated from the industrial evaporation process, micronutrient, and microbiological material, and to carry out a reaction of the organic substance, the micronutrient, and the microbiological material at a pH of about 6 to about 9 to form a bioreactor product. The system further comprises a purification arrangement configured to purify the water in the bioreactor product.

DETAILED DESCRIPTION OF THE INVENTION

Figure 1:
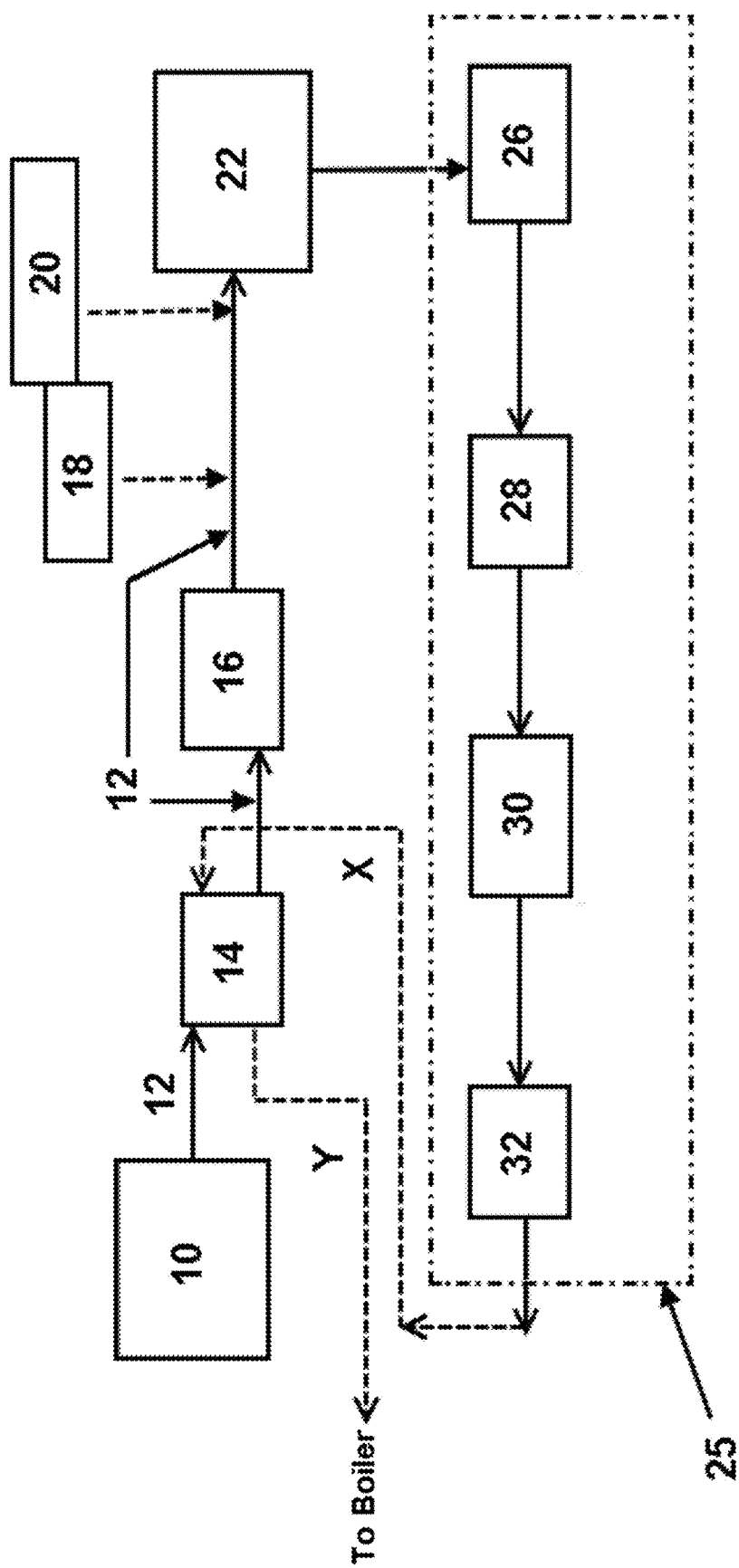
FIG. 1 is a flow diagram of an embodiment of a method and system as provided herein.

A method of removing organic substance from condensate generated from an industrial evaporation process is provided. The condensate comprises water and the organic substance. The method comprises combining the condensate with micronutrient and microbiological material to form treated condensate comprising water, the organic substance, the micronutrient, and the microbiological material; reacting the organic substance and the micronutrient with the microbiological material in the treated condensate at a pH of from about 6 to about 9 to form a bioreactor product comprising byproduct and water; and purifying the water from the byproduct in the bioreactor product to form purified water.

For purposes of the present disclosure, an industrial evaporation process is a process that separates combined liquid substances via heating into a bottoms liquid and a vapor. Generally, an industrial evaporation process is a somewhat crude separation process, removing a large portion of unwanted substance from a desired substance. However, both the bottoms liquid and the vapor are generally not 100% pure. For the methods and systems provided herein, the vapor is condensed into condensate rich with enthalpy and having variable purity. Should the water in the condensate be contaminated with an unacceptable amount of organic substance, the condensate may undergo the methods described herein, thereby permitting the purified water to be used as a feed stream of (e.g., recycled into) an industrial process.

In certain embodiments of the methods and systems provided herein, the industrial evaporation process is a food-related evaporation process. Examples of food-related evaporation processes include, but are not limited to, a sugar cane juice evaporation process, a dairy evaporation process, a coffee processing evaporation process, a fruit juice evaporation process, or a soup evaporation process. As can be seen from the aforementioned list, the term "food-related evaporation process" should be construed to include beverage-related evaporation processes. In certain embodiments of the methods and systems provided herein, the industrial evaporation process is at least one of a sugar cane juice evaporation process, a dairy evaporation process, a coffee processing evaporation process, a fruit juice evaporation process, a soup evaporation process, and a chemical industry evaporation process.

Certain embodiments of the methods provided herein further comprise, upstream of the combining step, subjecting the condensate to heat exchange to recover enthalpy from the condensate. In certain embodiments, the enthalpy from the condensate is recovered by subjecting the purified water produced by the methods described herein to heat exchange to pass enthalpy from the condensate into the purified water to form enthalpy-rich purified water. Certain embodiments of the methods provided herein further comprise feeding the purified water (e.g., the enthalpy-rich purified water) into a steam-generating system (e.g., a boiler system). In other embodiments, the enthalpy is recovered in a process stream of an industrial process.

Certain embodiments of the methods provided herein further comprise gathering the condensate in a vessel upstream of the combining step, but, when present, generally after being subjected to heat exchange. When utilized, the gathering step allows for combining one or more condensate streams and generally provides a relatively uniform feed stream to the steps downstream as compared to in the absence of a gathering stream.

As described herein, the condensate generated from industrial evaporation processes can be of variable purity. A relatively small amount of organic substance present in the condensate can cause the condensate to be unsuitable as a source of feed water. For example, boiler feed water should include less than about 5 ppm organic substance (measured as chemical oxygen demand), with zero organic substance preferred. Without removal of the organic substance, the condensate would be required to be removed from the industrial process and treated as wastewater, thereby wasting a substantial amount of enthalpy. Removing the organic substance from the condensate while conserving enthalpy is generally beneficial.

The organic substance may be any organic substance that may be found in an industrial evaporation process and that may be present in the condensate thereof. Examples of organic substances that may be present in industrial evaporation condensate include, but are not limited to, volatile organic compounds (e.g., ethanol) and sugar (e.g., sugar cane juice, sucrose, fructose, etc.).

For the methods provided herein, the condensate generated from an industrial evaporation process is combined with each of a micronutrient and a microbiological material to form treated condensate comprising water, the organic substance, the micronutrient, and the microbiological material. Any suitable method of combining the condensate with the micronutrient and the microbiological material may be utilized. For example, the condensate, the micronutrient, and the microbiological material (i.e., the components) may be placed in a bioreactor and mixed, so as to facilitate contact among the components. The components may be mixed or unmixed. The components may be mixed via any suitable form of mixing known in the art. For example, the components may be mixed via an impeller immersed in the bioreactor, via turbulence caused by aeration, or via pumps that circulate treated condensate in the bioreactor or between multiple bioreactors.

The microbiological material may be any suitable microbiological material that reacts with (e.g., consumes) the organic substance and the micronutrient. Examples of suitable microbiological materials include, but are not limited to, viruses, bacteria, protozoa, and fungi. In certain embodiments of the methods provided herein, the microbiological material is aerobic microbiological material. In certain embodiments of the methods provided herein, the microbiological material comprises bacteria. In certain embodiments of the methods provided herein, the microbiological material is selected from coccus, diplococcus, bacillus, tetrad, staphylococcus, streptococcus, filamentous, spirillum, spirochaetes, vibrio, and combinations thereof.

The micronutrient may be any suitable micronutrient that reacts with (e.g., is consumed by) the microbiological material and facilitates growth and/or multiplication of the microbiological material. Examples of suitable micronutrients include, but are not limited to, a composition comprising a bio-available form of an element selected from potassium, nitrogen, calcium, magnesium, iron, and combinations thereof.

In embodiments of the methods provided herein, the micronutrient and the organic substance are reacted with (e.g., consumed by) the microbiological material. In certain embodiments of the methods provided herein, the reaction is carried out at a pH of from about 6 to about 9.

The reaction of the micronutrient and the organic substance with the microbiological material forms a bioreactor product, which comprises byproduct and water. The bioreactor product is generally slimy and translucent with slight yellowish color when the bioreactor product is concentrated and/or partially dried. Generally, the byproduct may comprise microbiological metabolic excretion, microbiological material, unreacted micronutrient, and/or microbiological secretion.

The water is purified from the byproduct of the bioreactor product to form purified water. Generally, a sufficient amount of the byproduct can be separated from the water via one or more of various purification techniques, including, but not limited to, membrane filtration, polishing, reverse osmosis filtration, degassing, activated carbon filtration, mixed bed resin filtration, and combinations thereof.

Generally, purified water is of a purity that can be utilized in other industrial processes. In certain embodiments of the methods provided herein, the purified water is sufficiently pure to be utilized at a feed stream of a steam-generating system (e.g., a boiler system). In certain embodiments of the methods provided herein, the purified water has a chemical oxygen demand of less than about 5 ppm. In certain embodiments of the methods provided herein, the purified water has a total dissolved solids content of less than about 1 ppm. In certain embodiments of the methods provided herein, the purified water has a chemical oxygen demand of less than about 5 ppm and a total dissolved solids content of less than about 1 ppm.

In certain embodiments of the methods provided herein, the purifying of the water present in the bioreactor product comprises subjecting the bioreactor product to membrane filtration to form membrane filtered bioreactor filtrate. In certain embodiments of the methods provided herein, the membrane filtered bioreactor filtrate is purified water as described herein. For example, subjecting the bioreactor product to membrane filtration may provide purified water of sufficiently pure to be utilized at a feed stream of a steam-generating system (e.g., a boiler system).

In certain embodiments of the methods provided herein, the purifying of the water present in the bioreactor product further comprises subjecting the membrane filtered bioreactor filtrate to polishing. In certain embodiments of the methods provided herein, the polishing comprises subjecting the membrane filtered bioreactor filtrate to at least one of reverse osmosis filtration, degassing, activated carbon filtration, and mixed bed resin filtration. In certain embodiments of the methods provided herein, the polishing comprises subjecting the membrane filtered bioreactor filtrate to reverse osmosis filtration, degassing, activated carbon filtration, and mixed bed resin filtration.

A system for removing organic substance from condensate generated by an industrial evaporation process is provided. The condensate comprises water and the organic substance. The system comprises a bioreactor configured to receive the condensate generated from the industrial evaporation process, micronutrient, and microbiological material, and to carry out a reaction of the organic substance, the micronutrient, and the microbiological material at a pH of about 6 to about 9 to form a bioreactor product comprising byproduct and water; and a purification arrangement configured to purify the water in the bioreactor product.

In certain embodiments of the systems provided herein, the bioreactor is configured to receive each component (condensate, micronutrient, and microbiological material) individually or in any combination. In certain embodiments of the systems provided herein, the bioreactor is configured to receive all three components as a single combined substance (e.g., treated condensate). Generally, the bioreactor is configured to carry out at least the reacting step of the methods described herein.

In certain embodiments of the systems provided herein, the purification arrangement comprises a membrane filtration unit configured to receive the bioreactor product and provide a membrane filtered bioreactor filtrate. In certain embodiments of the systems provided herein, the purification arrangement further comprises a polishing arrangement to polish the membrane filtered bioreactor filtrate. In certain embodiments of the systems provided herein, the polishing arrangement comprises at least one of reverse osmosis filtration, degassing, activated carbon filtration, and mixed bed resin filtration, configured to receive the membrane filtered bioreactor filtrate and form purified water. In certain embodiments of the systems provided herein, the polishing arrangement comprises reverse osmosis filtration, degassing, activated carbon filtration, and mixed bed resin filtration, configured to receive the membrane filtered bioreactor filtrate and form purified water.

Certain embodiments of the systems provided herein further comprise a vessel configured to gather and deliver the condensate to the bioreactor. Generally, when present, the vessel is configured to carry out the gathering step of the methods described herein.

Certain embodiments of the systems provided herein further comprise a micronutrient delivery apparatus configured to deliver micronutrient to the condensate. The micronutrient delivery apparatus may be configured to provide an amount of micronutrient, for example, that an operator believes to be sufficient to drive the reaction (e.g., consumption) of the organic substance by the microbiological material, or the micronutrient delivery apparatus may be configured to deliver a precise amount of micronutrient, for example, based upon data gathered while practicing the methods described herein.

Similarly, certain embodiments of the systems provided herein further comprise a microbiological material delivery apparatus configured to deliver microbiological material to the condensate. The microbiological material delivery apparatus may be configured to provide an amount of micronutrient, for example, that an operator believes to be sufficient to drive the reaction (e.g., consumption) of the organic substance and the micronutrient, or the microbiological material delivery apparatus may be configured to deliver a precise amount of microbiological material, for example, based upon data gathered while practicing the methods described herein.

Certain embodiments of the systems provided herein further comprise a heat exchanger configured to recover enthalpy from the condensate, which may be further configured to pass enthalpy from the condensate into the purified water. Generally, utilization of the systems provided herein is intended to conserve enthalpy. A heat exchanger configured to recover enthalpy from the condensate and pass enthalpy from the condensate into the purified water provides an added level of enthalpy recovery.

FIG. 1 shows a flow chart of an exemplary embodiment of the methods and systems provided herein. In FIG. 1, industrial evaporation process 10 generating condensate stream 12, which feeds into and passes through heat exchanger 14 (optional). The configuration shown in FIG. 1 allows enthalpy to pass from condensate stream 12 into purified water stream X to form enthalpy-rich purified water Y. Purified water stream X and/or enthalpy-rich purified water stream Y can be fed into a steam-generating system (e.g., a boiler system). Condensate stream 12, as shown leaving heat exchanger 14, is fed into vessel 16 (optional) configured to gather and deliver the condensate to bioreactor 22.

Bioreactor 22 is a membrane bioreactor, thus bioreactor 22 is configured to receive the condensate generated from the industrial evaporation process, micronutrient, and microbiological material, and to carry out a reaction of the organic substance, the micronutrient, and the microbiological material at a pH of about 6 to about 9 to form a bioreactor product, and also to carry out at least a portion of the purification (i.e., be part of the purification arrangement configured to purify the water in the bioreactor product). As shown in FIG. 1, condensate stream 12 leaving vessel 16 is configured with pH adjustment apparatus 18 and micronutrient delivery apparatus 20, with the microbiological material being present in bioreactor 22, e.g., via delivery by hand.

As described above, bioreactor 22 is equipped with a membrane filter that is utilized to subject the bioreactor product to membrane filtration to form membrane filtered bioreactor filtrate, which exits bioreactor 22 and is delivered to polishing arrangement 25. As shown in FIG. 1, polishing arrangement 25 comprises reverse osmosis filtration 26, degassing 28, activated carbon filtration 30, and mixed bed resin filtration 32. One should recognize that a system for removing organic substance from condensate generated by an industrial evaporation process may not need each polishing unit operation shown in FIG. 1. Factors that may influence the selection of unit operations in the polishing arrangement include, but are not limited to, turbidity of the condensate, total organic carbon of the condensate, chemical oxygen demand of the condensate, and/or total dissolved solids of the condensate.

Purified water stream X shown leaving mixed bed resin filtration 32, as described above, may be fed to an industrial process, e.g., a steam-generating system (e.g., boiler system), or as shown in FIG. 1, may be passed through heat exchanger 14 configured to pass enthalpy from condensate stream 12 into purified water stream X to form enthalpy-rich purified water stream Y, which may be fed to an industrial process, e.g., a steam-generating system (e.g., a boiler system).

The following example further illustrates the invention but, of course, should not be construed as in any way limiting its scope.

EXAMPLE

Figure 2:
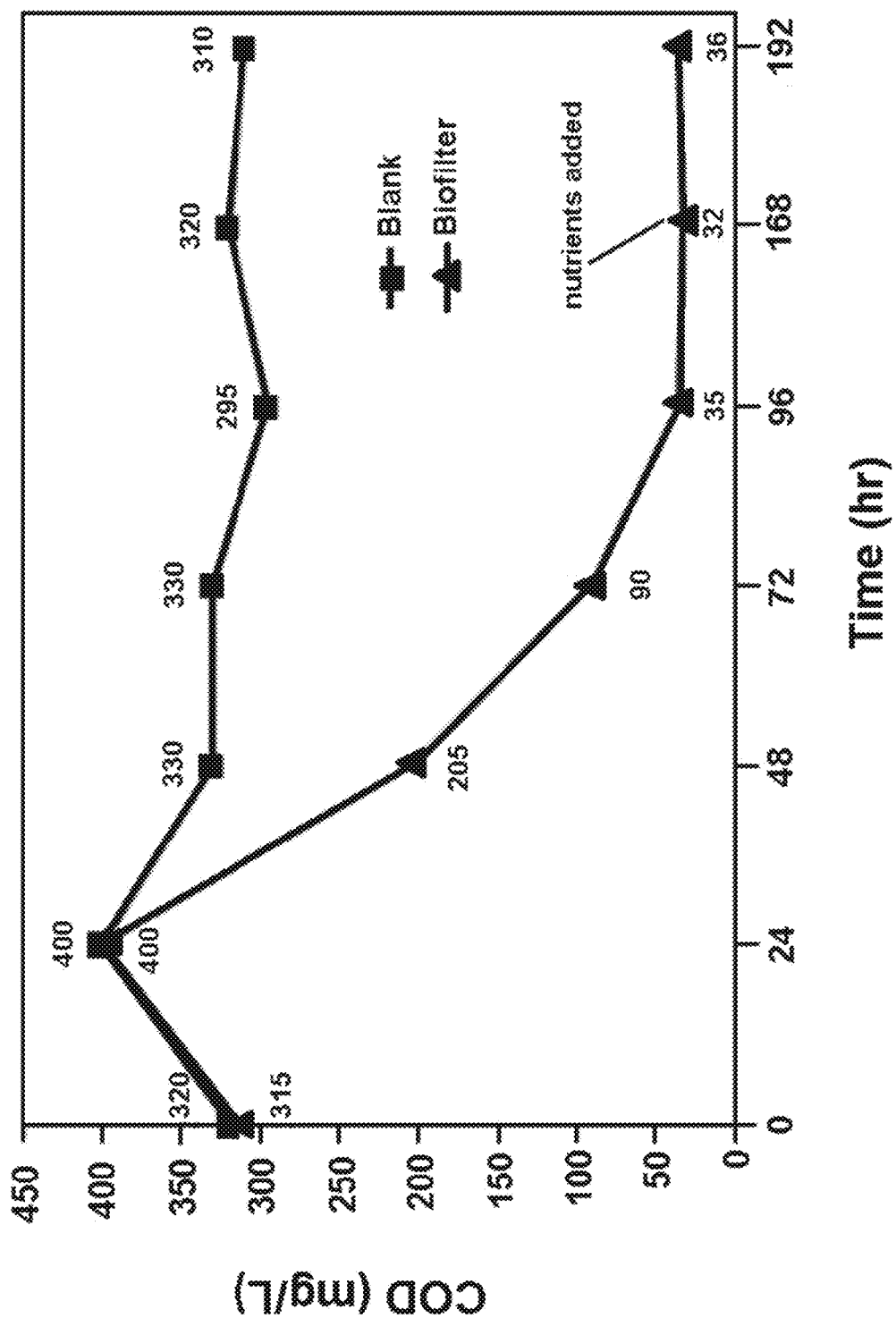
FIG. 2 is a graphical illustration of the results of Example 1 described herein.

Condensate generated from an industrial evaporation process and comprising water and an organic substance was combined with aerobic bacteria only (FIG. 2, control) and with aerobic bacteria and micronutrient (FIG. 2, experimental). The organic substance present in the condensate was evident by its chemical oxygen demand being 310 ppm. The aerobic bacteria for each of the runs was a random mixture of many different types of microbiological material: virus, bacteria, protozoa, fungi, and unknown microorganisms that may have grown in the bioreactor because of exposure to air. The micronutrient comprised dipotassium hydrogen orthophosphate ($K_2HPO_4$), ammonium chloride ($NH_4Cl$), calcium chloride dihydrate ($CaCl_2.2H_2O$), magnesium sulfate heptahydrate ($MgSO_4.7H_2O$), and ferric chloride hexahydrate ($FeCl_3.6H_2O$) as shown in Table I below.

| Element | Atomic Wt. (g/mole) | Reagent | Molecular weight (g/mole) | Element ppm | Reagent ppm |
|---|---|---|---|---|---|
| P | 30.97 | $K_2HPO_4$ | 174.18 | 1.5 | 8.44 |
| N | 14.01 | $NH_4Cl$ | 53.49 | 7.5 | 28.64 |
| Ca | 40.08 | $CaCl_2 \cdot 2H_2O$ | 147.02 | 0.75 | 2.75 |
| Mg | 24.31 | $MgSO_4 \cdot 7H_2O$ | 246.48 | 0.75 | 7.6 |
| Fe | 55.85 | $FeCl_3 \cdot 6H_2O$ | 270.30 | 0.75 | 3.63 |

The components were reacted over time, with each of the bioreactor products (control and experimental) being subjected to membrane filtration to form membrane filtered bioreactor filtrate. The chemical oxygen demand of the membrane filtered bioreactor filtrate is shown in FIG. 2 over time. As shown in FIG. 2, the utilization of micronutrient in the reaction led to a dramatic drop in chemical oxygen demand (nearly 90%) over time in the membrane filtered bioreactor filtrate leaving the membrane bioreactor.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of removing a sugar from condensate generated from a food-related evaporation process, the condensate comprising water and the sugar, the method comprising: combining the condensate with nutrient and a microorganism to form treated condensate comprising water, the sugar, the nutrient, and the microorganism;
reacting the sugar and the nutrient with the microorganism in the treated condensate at a pH of from about 6 to about 9 to form a bioreactor product and water; and
purifying the water from the bioreactor product to form purified water;
wherein, upstream of the combining step, the condensate is subjected to a heat exchange to recover enthalpy from the condensate; and
wherein the purified water has a chemical oxygen demand of less than about 5 ppm.

2. The method of claim 1, wherein the food-related evaporation process is at least one of a sugar cane juice evaporation process, a dairy evaporation process, a coffee processing evaporation process, a fruit juice evaporation process, or a soup evaporation process.

3. The method of claim 1, wherein the microorganism is at least one of a virus, a bacterium, a protozoan, or a fungus.

4. The method of claim 1, wherein the nutrient comprises a composition comprising a bio-available form of an element selected from potassium, nitrogen, calcium, magnesium, iron, and combinations thereof.

5. The method of claim 1, further comprising gathering the condensate upstream of the combining step.

6. The method of claim 1, further comprising subjecting the purified water to heat exchange to pass enthalpy from the condensate into the purified water to form enthalpy-rich purified water.

7. The method of claim 6, further comprising feeding the enthalpy-rich purified water into a steam-generating system.

8. The method of claim 1, wherein the purifying of the water from the bioreactor product comprises subjecting the bioreactor product to membrane filtration to form membrane filtered bioreactor filtrate.

9. The method of claim 8, wherein the purifying of the water from the bioreactor product further comprises subjecting the membrane filtered bioreactor filtrate to at least one of reverse osmosis filtration, degassing, activated carbon filtration, and mixed bed resin filtration.

10. A system for removing a sugar from condensate generated by a food-related evaporation process, the condensate comprising water and the sugar, the system comprising:
a heat exchanger configured to recover enthalpy from the condensate generated from the food-related evaporation process;
a bioreactor configured to receive the condensate from the heat exchanger, a nutrient, and a microorganism, and to carry out a reaction of the sugar, the nutrient, and the microorganism at a pH of about 6 to about 9 to form a bioreactor product; and
a purification arrangement configured to purify the water from the bioreactor product,
wherein the purification arrangement comprises a membrane filtration unit configured to receive the bioreactor product and to provide a membrane filtered bioreactor filtrate, and a polishing arrangement to subject the membrane filtered bioreactor filtrate to at least one of reverse osmosis filtration, degassing, activated carbon filtration, and mixed bed resin filtration, and
wherein the purified water has a chemical oxygen demand of less than about 5 ppm.

11. The system of claim 10, further comprising a nutrient delivery apparatus configured to deliver nutrient to the condensate.

12. The method of claim 1, wherein the microorganism is an aerobic microorganism.

13. The method of claim 1, wherein the microorganism is a bacterium.

14. The method of claim 1, wherein the microorganism is selected from coccus, diplococcus, bacillus, tetrad, staphylococcus, streptococcus, filamentous, spirillum, spirochaetes, vibrio, and combinations thereof.

15. The system of claim 10, wherein the microorganism is an aerobic microorganism.

16. The system of claim 10, wherein the microorganism is a bacterium.

\* \* \* \* \*